United States Patent [19]

Loesche

[11] Patent Number: 5,116,735
[45] Date of Patent: May 26, 1992

[54] DIAGNOSING PERIODONTAL DISEASE BY MEASURING PROTEOLYTIC ACTIVITY OF PERIODONTOPATHOGENIC BACTERIA

[75] Inventor: Walter J. Loesche, Ann Arbor, Mich.

[73] Assignee: The University of Michigan, Ann Arbor, Mich.

[21] Appl. No.: 634,924

[22] Filed: Dec. 24, 1990

Related U.S. Application Data

[63] Continuation of Ser. No. 385,977, Jul. 26, 1989, abandoned, which is a continuation of Ser. No. 56,596, Jun. 1, 1987, abandoned, which is a continuation-in-part of Ser. No. 740,097, May 31, 1985, abandoned.

[51] Int. Cl.$^5$ .................. C12Q 1/04; C12Q 1/02; G01N 33/48; C12N 1/20
[52] U.S. Cl. ........................................ 435/34; 424/2; 435/21; 435/23; 435/29; 435/252.4
[58] Field of Search ................ 435/21, 23, 28, 29, 435/34, 37, 252.4; 424/2

[56] References Cited

U.S. PATENT DOCUMENTS

| | | | |
|---|---|---|---|
| 4,397,944 | 8/1983 | Komura et al. | 435/34 X |
| 4,568,535 | 2/1986 | Loesche | 514/365 X |
| 4,582,795 | 4/1986 | Shibuya et al. | 435/34 |
| 4,591,554 | 5/1986 | Koumura et al. | 435/34 X |
| 4,603,108 | 7/1986 | Bascomb | 435/34 |

FOREIGN PATENT DOCUMENTS 0165905 12/1985 European Pat. Off. .............. 435/34

OTHER PUBLICATIONS

Ames Company, Chart of Instructions for Microstrix-3, Division of Miles Laboratories, Inc. 1976.

*Primary Examiner*—David M. Naff
*Attorney, Agent, or Firm*—Rohm & Monsanto

[57] ABSTRACT

A colorimetric assay for diagnosis of periodontal disease is carried out by using a chromogenic test substance which is hydrolyzed by trypsin-like enzymes produced by periodontopathogenic bacteria in a sample specimen of subgingival plaque to release a chromophore. The presence of periodontal disease is thus indicated by a color change. The results of this assay are reliable provided at least a minimum number of microorganisms, on the order of 1,000,000 to 10,000,000, are present in the specimen. This assay determines whether the specimen includes the requisite number of microorganisms so that false negative results are not occasioned as a result of inadequate specimen size. Enzymatic activity of microorganisms in the specimen, illustratively phosphatase or peptidase enzymes, indicates specimen size sufficiency by the release of a chromophore from a nonspecific chromogenic test substance.

27 Claims, No Drawings

DIAGNOSING PERIODONTAL DISEASE BY MEASURING PROTEOLYTIC ACTIVITY OF PERIODONTOPATHOGENIC BACTERIA

RELATIONSHIP TO OTHER APPLICATION

This patent application is a continuation of U.S. Ser. No. 385,977, now abandoned, filed Jul. 26, 1989, which was a continuation of U.S. Ser. No. 056,596, now abandoned, filed Jun. 1, 1987 by the same inventor as herein and assigned to the same assignee, which is a continuation-in-part of U.S. Ser. No. 740,097, now abandoned, filed May 31, 1985, in which the inventor herein is a coinventor, and which is assigned to the same assignee as herein.

BACKGROUND OF THE INVENTION

This invention relates generally to systems for diagnosing oral diseases in mammals, and more particularly, to a colorimetric diagnostic test for periodontal disease activity in a human being, or an animal.

Periodontal disease is the major affliction of the human dentition. Today, more teeth are lost to the effects of periodontal disease than to caries (tooth decay). Periodontal disease is a group of conditions affecting the gingiva (gum) and the bones that support the teeth. The primary cause of periodontal disease is bacterial plaque which causes an inflammation of the gum which may result in actual destruction of tissue. In some cases, destruction of the bone occurs to the point where teeth lose their attachment thereto.

In periodontal disease, there is usually a large accumulation of bacteria in plaque attached to the tooth, both above (supragingival) and below (subgingival) the gum line. This plaque can become calcified in its depths, forming what is known as calculus. This plaque and associated calculus can create a pocket between the teeth and the gingiva which is characteristic of the disease. Presently, periodontal disease is diagnosed by clinical observation of indicators such as the presence and depth of pockets, loss of attachment of the teeth to the bone, and papillary bleeding of the gums. Clinical observations, however, are not always reliable indicators. For example, deep pockets are not necessarily infected by bacteria capable of causing inflammatory tissue destruction (periodontopathic bacteria). Unfortunately, there are currently no reliable, inexpensive, and objective means for determining whether or not the pocket is infected with periodontopathic bacteria.

The lack of a diagnostic test has been a serious problem, particularly in view of the severity of the corrective measures typically required to be taken to treat periodontal disease. Such measures can include, the excising of diseased gum tissue so as to expose and debride affected roots and to eliminate pockets. Recently, more conservative surgical treatment has been developed which typically involves detaching a flap of gum from the tooth, cleaning the freshly exposed tooth surface of all calculus and plaque, and then suturing the gingiva back together over the cleaned surface. Both surgical approaches work equally well as long as the patient continues to have professional maintenance treatment.

Although periodontal disease has traditionally been defined as an inflammation of the gums, which means that host tissue is responding to bacteria and/or the products of bacteria, periodontal disease has not been treated like a bacterial infection in the medical sense. For example, periodontal disease has not been treated in the art with antimicrobial drugs because the growth of plaque on the teeth appears to be inevitable and since it is external to the body, would not seem to be treatable by systemically administered drugs. Moreover, it was not believed that periodontal disease was specific to one, or several, particularly damaging bacteria. In fact, about 200 species of microbes have been isolated from various plaque samples. Thus, mechanical treatment which requires instrumenting of the tooth to remove accumulated bacterial deposits non-specifically was deemed to be the appropriate means of treating periodontal disease.

It has been reported that periodontal disease is characterized by a progressive loss of tooth supporting tissue which occurs when the periodontal pocket is colonized by a preponderance of gram negative anaerobic bacteria (see, e.g., Loesche, et al., "Role of Spirochetes in Periodontal Disease," *Host-Parasite Interaction in Periodontal Disease*, Genco and Mergengagen, eds., American Society of Microbiology, Washington, D.C., 1982, pages 62–75 and Slots, "Importance of Black Pigmented Bacteroides in Human Periodontal Disease," Ibid., pages 27–45). Spirochetes and black pigmented bacteroides (BPB) are particularly prominent when pockets bleed upon probing and when there is clinical evidence of disease progression. Thus, the possibility of drug treatment directed towards these anaerobic organisms is raised. In fact, beneficial results have been observed with the use of metronidazole, an antimicrobial effective against anaerobes. Metronidazole is available under the trademark FLAGYL from G. D. Searle & Co., Chicago, Ill. 60680 as well as in generic form from Zenith Laboratories, Inc., Ramsey, N.J. The use of drugs, in the treatment of periodontal disease has accentuated the need for an objective means of detecting the presence of anaerobic periodontal infection since some of the clinical symptoms, such as pockets, will still be observable in drug-treated patients, but may not necessarily be infected. Thus, there exists a need in the art for a simple, reliable test for monitoring the efficacy of drug therapy.

Bacteriological diagnosis of elevated levels of spirochetes and BPB by cultural methods can only be done in the research laboratory at the present time. Certain types of the spirochetes, however, cannot be grown in a culture with existing technology.

The spirochetes can be diagnosed by microscopic examination using either phase contrast or dark field condensers. One prior art technique used for the diagnosis of periodontal disease involves the microscopic examination of the plaque for determination of the presence of motile forms, mostly spirochetes, and thereby assesses the need for escalating or terminating therapy [see, Keyes, et al., "Diagnosis of Creviculoradicular Infections," Ibid., pages 394–403 and Listgarten, et al., *J. Clin. Periodontal.*, Vol. 8, pages 122–138 (1981]. However, no similar microscopic procedure exists for the identification of BPB. Thus, the dentist/clinician must presently resort to the purchase of expensive microscopes and associated video equipment and/or have available sophisticated research laboratory facilities in order to make necessary assays and measurements for the presence or absence of bacteriological parameters that correlate to periodontal disease.

In view of the present state of the art, there is a great need for a reliable and inexpensive test system for identifying the presence of periodontal disease activity due to anaerobic bacteria. There is additionally a need for a test system which can conveniently be performed by a dentist/clinician. Such a test system would be of significant value in advising a patient of his or her condition, as well as monitoring the effectiveness of treatment.

In a previous patent application, U.S. patent application Ser. No. 740,097 filed May 31, 1985 and assigned to the assignee hereof, a simple and inexpensive diagnostic test for periodontal disease is described wherein the proteolytic activity of a specimen of suspected periodontopathogenic bacteria is measured. More specifically, this assay method operates to detect the presence of trypsin-like activity, illustratively in a specimen of subgingival plaque. In one embodiment of that invention, a chromogenic test substance comprises an amino acid or a peptide substrate combined with a chromosphore which is hydrolyzable by trypsin-like enzymes in the specimen to release a chromophore. Detection of a color change due to said release indicates whether such trypsin-like activity is present, and hence, whether or not periodontal disease is present.

One problem with the aforementioned technique is that a minimum number of microorganisms should be present in the specimen in order for the results of the test to be a reliable indication of the presence of periodontopathic organisms. It is a feature of the invention described in U.S. patent application Ser. No. 740,097 that the sample size, or content, does not have to be quantified or measured. This aspect of that invention contributes significantly to its simplicity. However, color development is a function of the total number of bacteria which possess the trypsin-like enzyme that are present in the sample. Thus, if the specimen itself is small, and consequently contains less than the minimum number of such microorganisms, then the test procedure may produce a false negative result even though periodontal disease-producing microorganisms are present in the specimen.

Accordingly, it is an object of this invention to provide an improved diagnostic test for determining the presence of periodontal disease.

It is another object of the invention to provide a diagnostic test system which can identify periodontal disease and which does not require clinical observation so that the disease can be detected at an incipient stage at which it is not yet clinically observable.

It is a further object of the invention to provide a diagnostic test for detecting the presence of, inter alia, Treponema denticola, Bacteroides gingivalis, Bacteroides forsythus, Capnocytophaga gingivalis and other organisms in the plaque which possess trypsin-like enzyme activity.

It is also an object of the invention to provide a diagnostic test for periodontal disease which can be performed in the office of a dentist/clinician by unskilled personnel, and which does not require expensive or special equipment.

It is an additional object of the invention to provide a diagnostic test for periodontal disease which is reliable.

It is a further additional object to provide a diagnostic test for periodontal disease which yields an indication of the reliability of the diagnostic test results for a particular patient.

It is yet another object of the invention to provide a diagnostic test for periodontal disease which can be used to monitor the virulence of infection.

It is yet a further object of the invention to provide a diagnostic test for periodontal disease which can be performed easily as part of a patient's regular periodic check-up, for epidemiological surveys, for screening examinations, such as military screening, and for monitoring treatment efficacy on periodontal patients.

It is still another object of the invention to provide a diagnostic test for periodontal disease which is capable of detecting anaerobic bacteria under aerobic conditions.

It is still another object of the invention to provide a diagnostic test for periodontal disease which does not require culturing of bacterial specimens, and which will test directly a sample of plaque or other such specimen.

It is additionally an object of the invention to provide a convenient assay kit which can be used in the diagnosis of periodontal disease.

It is additionally a further object of the invention to provide a colorimetric diagnosis system where by the presence of periodontal disease is determined by a color change.

SUMMARY OF THE INVENTION

The foregoing and other objects, features, and advantages are achieved by this invention which provides an improved diagnostic test for periodontal disease of the type described in U.S. patent application Ser. No. 740,097. The method of diagnosis of U.S. patent application Ser. No. 740,097, the specification of which is incorporated herein by reference, comprises the steps of sampling bacterial flora from the oral cavity of a mammal, illustratively a human being, and then measuring the proteolytic activity of the sample with a chromogenic test substance. In particular, a trypsin-like activity is measured since periodontopathogenic organisms, such as T. denticola, B. gingivalis, B. forsythus, and C. gingivalis, are characterized by such activity. In accordance with the present invention, the specimen is additionally assayed for a nonspecific enzymatic marker for indicating whether the specimen contains a predetermined minimum number of microorganisms sufficient to yield a reliable test result.

Analysis of the results of extensive testing has revealed that a population of approximately between 1 and 10 million bacteria in the specimen is sufficient to yield reliable results with the proteolytic enzyme test. However, if the specimen itself is small, having a bacterial population illustratively on the order of less than one million bacteria, then the test procedure may yield a negative result solely because there were too few bacteria in the specimen.

Some enzymes appear to be possessed by most, if not all, members of the oral flora. The measurement of the activity of these common nonspecific enzymes can be used as an indicator of the presence of microorganisms per se, and hence, of specimen size sufficiency. This invention provides a second chromophore-containing test substance which is enzymatically degradable by the nonspecific marker enzyme to release a chromophore thereby producing an observable color change when at least a predetermined number of microorganisms are present in the sample.

In one illustrative embodiment, the nonspecific enzymatic marker is a phosphatase which is present in most, if not all, bacteria found in the flora of the oral cavity. If the phosphatase enzyme reacts with a second chromogenic test substance to give a positive result, then there are enough organisms in the sample to give a true, reliable test result for the trypsin-like enzyme test. On the other hand, if the phosphatase test is negative, a negative trypsin-like enzyme test would be expected. The clinician is thereby immediately alerted that the sample is too small and that he or she should resample the patient.

Specific illustrative examples of second chromogenic test substances which are enzymatically degradable by phosphatase enzymes include para- and ortho-nitrophenol phosphates, which give good results with alkaline phosphatase, and o-carboxyphenol phosphate which gives good results with acid phosphatase.

In another illustrative embodiment, the nonspecific enzymatic marker is a peptidase, and more specifically an aminopeptidase. An exemplary second chromogenic test substance which is enzymatically degradable by an aminopeptidase is L-proline-$\beta$-naphthylamide.

These second chromogenic test substances can be combined with the test substances described in U.S. patent application Ser. No. 740,097. Specific examples given therein for measuring trypsin-like activity of suspected periodontopathogenic bacteria are N-benzoyl-DL-arginine-2-naphthylamide (BANA) and benzoyl-DL-arginine-nitroanilide (BAPNA).

The only criterion for selecting a combination of chromogenic test substances is that the color changes produced by release of the respective chromophores must be distinguishable from one another. Thus, as will be described more completely hereinbelow, if BANA is used to measure trypsin-like activity, the substrates which are hydrolyzable by phosphatases to release a chromophore are color compatible and may advantageously be used as the second test substance. If BAPNA is used to measure trypsin-like activity, L-proline-$\beta$-naphthylamide, which is hydrolyzable by an aminopeptidase, can advantageously be used as the second test substance. In certain embodiments, a color developer is added to produce the color change responsive to enzymatic activity.

DETAILED DESCRIPTION OF THE INVENTION

The invention described in U.S. patent application Ser. No. 740,097 is a simple, inexpensive diagnostic tool for periodontal disease which a dentist/clinician can use as part of an in-office routine. The laboratory culturing and microscopic techniques used in the taxonomic screening, described hereinabove and in the referenced prior art, cannot generally be conducted in the office of the practitioner. Specimens of plaque, for example, can contain the requisite amount of organisms to yield a positive enzymatic reaction in the technique described therein, if active periodontal disease exists. A sample as small as between 10 and 100 micrograms of infected plaque has been shown to yield a positive result. Thus, in accordance with that invention, a method of detecting or demonstrating elevated levels of microorganisms such as B. gingivalis or spirochetes in a plaque sample, gingival crevice fluid, tissue biopsy, or similar oral specimen, can be equated to positive diagnosis of an active periodontitis due to anaerobic bacteria. Thus, a clinician is able to advise a patient of the presence of infection and to commence a course of treatment which will reduce or suppress these organisms in the plaque. Additionally, the invention provides a simple system for monitoring the efficacy of therapeutic treatment.

The following is a brief recapitulation of a preferred embodiment of the invention of U.S. patent application Ser. No. 740,097: An oral specimen suspected of containing elevated levels of the organisms characteristic of periodontal disease is subjected to a chromophore-containing substrate specific to an enzyme produced by the suspected periodontal disease-producing organisms. T. denticola, B. gingivalis, B. forsythus, and the spirochetes produce a proteolytic enzyme and/or a peptidase which is capable of hydrolyzing the substrate, thereby releasing a chromophore as a reaction product. This released chromophore can then be colorimetrically observed. In certain embodiments, the addition of another chromogenic agent, or color developer is required. The presence or absence of a color in response to enzymatic conditions is correlated to elevated bacterial conditions related to active periodontal disease.

Among the bacterial species known to be associated with periodontal disease, the following species: T. denticola, a spirochete; B. gingivalis, the most virulent of the BPB; B. forsythus, an organism often isolated from sites of progressive destruction; and C. gingivalis, an organism associated with periodontal disease in diabetics; all possess a trypsin-like enzyme that can be measured by the hydrolysis of the trypsin substrate BANA. [see, Loesche, J. Oral Microbiol. Immunol., Vol. 1, Pages 65–70, (1986)]. At least 40 other plaque species are unable to hydrolyze the BANA substrate, but these species are not considered to be of primary importance in producing periodontal disease. Thus, the ability of the plaque to hydrolyze BANA can reflect the presence and/or proportional increase of one or more of these bacterial species in the plaque and therefore provides a measurement of an anaerobic infection in the periodontal plaque.

In a specific illustrative embodiment, the peptide substrate BANA is colorless. Upon incubation with bacteria in the specimen, the chromophore, $\beta$-naphthylamide, is released from its linkage with the carboxyl group of arginine. The subsequent addition of a color developer, such as fast garnet, results in the formation of a bright orange-red color if there is a high level of enzymatic activity in the specimen. The development of a yellow color is interpreted as a negative result. In an alternative advantageous embodiment, the peptide substrate is BAPNA which forms color as it hydrolyses, thereby obviating the need for an additional color developer to demonstrate the enzymatic activity of the specimen.

Of course, there are variations of colors between positive and negative test which can be interpreted as varying degrees of enzymatic activity, and as indicative of a condition which should be monitored by the dentist/clinician. Experience indicates that interpretation of the degree of color development in the colorimetric test system is readily amenable to the development of standardized color charts for comparison purposes to determine the presence or absence of enzymatic activity.

As previously stated, one of the features of the invention of U.S. patent application Ser. No. 740,097 which contributes to its simplicity and economy is that specimen size, or content, does not have to be separately quantified or measured. However, the test results are dependent upon a certain minimum level of microorganisms for color development. Extensive testing has shown that about 1,000,000 to 10,000,000 bacteria in the specimen will give reliable results in the enzyme test of U.S. patent application Ser. No. 740,097.

In the preferred embodiment of the improved diagnostic system of the present invention, a second chromogenic test substance is provided to demonstrate that the quantity of microorganisms in the specimen exceeds a predetermined number and is, therefore, sufficient to yield reliable results with the proteolytic enzyme test. Advantageously, the second chromogenic substrate is hydrolyzable by an enzyme which is present in most, if not all, bacteria found in the flora of the oral cavity so that it can be used as a measure of the quantity of microorganisms present in the specimen. In a preferred embodiment, enzymatic degradation of the second chromophore-containing substrate produces an observable color change if there are greater than about 1,000,000 microorganisms in the sample, or such other predetermined number as is necessary to give a true, reliable result with the proteolytic and/or peptidase enzyme test. The minimum predetermined number, of course, depends on the sensitivity of the chromogenic text substance to enzymatic degradation.

Phosphatase is an enzyme which is prevalent in the flora of the oral cavity. Both alkaline and acid phosphatase, depending upon the pH of the test solution, can be used as nonspecific markers of enzymatic action. A phosphatase is an enzyme that catalyzes the hydrolysis and synthesis of phosphoric acid esters and the transfer of phosphate groups from phosphoric acid to other compounds. Therefore, phosphate group-containing substrates such as o-nitrophenol phosphate which can be hydrolyzed by the action of phosphatase to release the chromophore nitrophenol are suitable as the second chromogenic test substances. Other illustrative examples are p-nitrophenol phosphate and o-carboxyphenol phosphate.

Of course, the activity of other enzymes commonly found in the bacterial flora of the oral cavity can be used in lieu of the phosphatase activity. Illustrative examples are the amino peptidases for proline, leucine, and phenylalanine. However, the second chromogenic substance chosen to be specific to the peptidase must not release a chromophore which will produce a color which will interfere with the ability of the clinician to observe the color change indicative of the trypsin-like activity of suspected periodontopathogenic bacteria. This can be achieved, for example, if the nitroanilide chromophore that is found in BAPNA is used and the $\beta$-naphthylamide derivative of proline is used as the second chromogenic test substance. In this case a negative reaction for BAPNA hydrolysis is colorless, whereas a positive reaction for proline hydrolysis is red-orange after the addition of fast garnet to the reaction mixture. It is, of course, obvious to anyone familiar with the art that other substrates containing a $\beta$-naphthylamide chromophore could be used as the chromogenic substrate.

In a specific illustrative embodiment, samples of plaque are removed with a sterile curette and suspended in an aqueous solution by vigorous agitation in a small, stoppered presterilized vial. A stock solution of BANA is prepared by dissolving 44 mg BANA (Sigma Chemical Company, St. Louis, Mo.) in 1 ml dimethyl sulfoxide (DMSO). Prior to use, the BANA stock solution is diluted with a 1:100 by volume mixture of 0.1 M Tris (hydroxymethyl) Aminomethane hydrochloride buffer at pH 8.5. The buffered BANA solution was added to the plaque sample and allowed to incubate overnight. The addition of a drop of fast garnet produced a color, within about 5 minutes.

Laboratory results indicate that the pH of the BANA-sample solution can range from between about 5.0 and 8.5. Other buffers, such as Sorenson phosphate buffer or a phosphate buffer with EDTA, can be used.

The results show that a nonbuffered solution in pure distilled water works as well as a buffered solution. Incubation generally requires a period of time ranging from about less than an hour to about 24 hours. Moreover, the incubation temperature should be in the range of about 25° C. to 45° C., and preferably approximately 37° C.

In a specific illustrative embodiment of the present invention, a second chromogenic test substance, p-nitrophenol phosphate (pNPP), is added to an aqueous, alkaline buffered solution containing the diagnostic reagent BANA, prepared as described above. In an alternative embodiment, BANA can be added after the pNPP reagent. The specimen is then added to the solution containing the reagents and the solution is incubated at about 37° C. Both reagents are initially colorless. However, the action of alkaline phosphatase from microorganisms in the specimen will liberate the chromophore p-nitrophenol. If a sufficient quantity of microorganisms are present in the sample, the solution will observably turn yellow. Upon the development of a yellow color the clinician performing the test is assured that the specimen size is adequate, and a color developer, e.g., fast garnet, is added to indicate whether the $\beta$-naphthylamide chromophore has been released from BANA by bacteria producing the trypsin-like enzyme. If so, an orange-red color will develop indicating the presence of periodontopathogenic organisms in the specimen. If the color remains yellow, then the presence of periodontopathic organisms is contraindicated. The clinician is therefore assured that the yellow color results from a lack of periodontopathic organisms and not because the specimen size is too small. Accordingly, the doubt which is present in the art in regard of a possible false negative result due to inadequate sample size is obviated.

The diagnosis of anaerobic periodontal infection resulting from spirochetes and/or *B. gingivalis, C. gingivalis, T. denticola,* and *B. forsythus,* by positive hydrolysis of BANA is also improved by the incorporation of o-nitrophenol phosphate (ONP). This results from the fact that ONP can be hydrolyzed by alkaline or acid phosphatases, depending on the pH of the reaction mixture, and is possessed by a wide variety of plaque bacteria and host cells that would be present in a plaque sample. The hydrolysis of ONP yields a positive result when about 1,000,000 bacteria are present in the sample. This number of bacteria corresponds to an approximately 10 $\mu$g sample of plaque (wet weight). All plaque samples containing 10 $\mu$g of plaque will exhibit a positive ONP test result. If a clinician removes a plaque sample that is so small it can hardly be seen with the naked eye, and adds it to BANA-ONP reaction mixture, the following sequence of color development occurs:

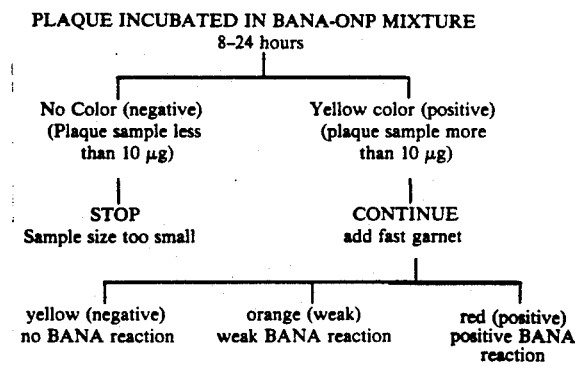

culated. The volume of one high power field is approximately $1.86 \times 10^{-6}$ ml.

TABLE I

| ENZYME DIAGNOSIS | No. of Plaques | ENZYME REACTIONS | | SPIROCHETES | CLINICAL | |
|---|---|---|---|---|---|---|
| | | ONP | BANA | | Diseased | Healthy |
| 1. Anaerobic Infection | 22 | + | + | 2.6/hpf | 22 | 0 |
| 2. Low Level Anaerobic Infection | 5 | + | weak | 2.1 | 4 | 1 |
| 3. No Infection | 7 | + | − | .8 | 1 | 6 |
| 4. No Infection But Sample Size Borderline | 12 | weak | − | .1 | 1 | 11 |
| 5. Sample Too Small (Discard) | 2 | − | − | 0 | | 2 |

| DIAGNOSIS | DIAGNOSIS | DIAGNOSIS |
|---|---|---|
| no anaerobic plaque infection | 1. Low Level anaerobic plaque infection | 1. Anaerobic plaque infection |
| | 2. Retreat if found following treatment | 2. Treat patient and/or site |
| | OTHERWISE repeat test or follow patient closely | |

A negative ONP reaction would tell the clinician that the plaque sample is too small to permit reliable diagnosis. The clinician would then either retake a sample from the patient, or depending upon the clinical appearance of the gingival tissue, not resample until the next visit. On the other hand, a positive ONP reaction indicates to the clinician that there is sufficient plaque in the sample to proceed with the addition of the fast garnet reagent. If there is no color change after the addition of the fast garnet, the clinician has diagnosed a nondiseased plaque relative to the presence of anaerobic organisms.

The following is illustrative of the findings obtainable using the combined BANA-ONP mixture: Plaque specimens were taken from 48 patients in a dental clinic and incubated overnight in the combination BANA-ONP mixture described hereinabove.

The results of the color reactions were compared with the clinical findings from examination of clinical symptoms such as papillary bleeding, pocket depth, and loss of attachment of the tooth to the bone and with the microscopic findings of spirochetes. The results are shown in Table I below. The clinician who diagnosed the patient did so without any knowledge of the enzyme test results.

With respect to the microscopic examination, 10 μl of sample dispersed in a buffer was placed on a glass slide under a 20×30 mm cover slip and sealed. It should be noted that the specimens for the microscopic examination were kept in an anaerobic chamber prior to examination by a Zeiss dark-field microscope. Twenty fields of the 100× oil immersion objective lens, or 200 bacteria, whichever came first, were counted. The number of spirochetes per high power field (hpf) was then cal- These results indicate clearly that the combined enzyme assay reliably reflects the clinical situation. All 22 plaques diagnosed by the enzyme reagents as being infected agreed with the clinical diagnosis of periodontal disease. In the 21 plaques in which the BANA enzyme reaction was negative (items 3-5), 19 of of these patients were diagnosed clinically as requiring no periodontal treatment. Two of these BANA enzyme negative samples (item 5) were discarded as being too small for analysis in correspondence with the o-nitrophenol phosphate test and indicated that the clinician should retest using a larger specimen.

In an alternative embodiment trypsin-like enzyme substrate comprises BAPNA and the second chromogenic test substance is N-L-proline-β-naphthylamide (PNA), the naphthylamide derivative for L-proline amino peptidase. Referring to the foregoing example, the BAPNA substrate is prepared as described for BANA and PNA was added thereto. The specimen is incubated with this mixture overnight. Development of a yellow color indicates an anaerobic infection. Failure of a color to develop is an equivocal result in that it indicates either that the specimen was too small or that there is no anaerobic infection. The addition of a color developer, such as fast garnet, solves the dilemma. The development of an orange to red color from the hydrolysis of PNA indicates that enough plaque was present in the sample. If a yellow color develops, then the plaque sample was too small. This is illustrated in the following diagram:

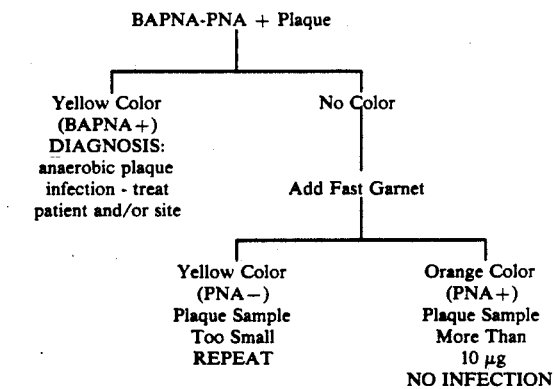

Of course, other chromogenic test substances can be substituted for those described herein, as long as the color developed by the nonspecific enzyme reaction does not interfere with the color developed as a result of the specific trypsin-like enzyme reaction. An additional specific example is o-carboxyphenol phosphate which is a substrate for acid phosphatase and the β-naphthylamide derivatives of L-leucine and L-phenylalanine.

It is to be understood, however, that other chromophore-containing substrates can be used in the practice of the invention. Since trypsin attacks proteins at arginine or lysine, it is apparent that other peptide/chromophore combinations involving these basic amino acids, could be substituted for BANA or BAPNA. Illustrative examples are the stereoisomeric analogues of the BANA and BAPNA compounds described hereinabove, such as L-BANA and L-BAPNA. *T. denticola* and some *B. gingivalis* strains are active in vitro against L-pyrrolidonyl-β-naphthylamide, so that this non-peptide chromophore may be of value in the diagnosis of anaerobic periodontal infections. All peptide chromophores, mentioned herein, can be purchased from chemical supply houses such as Sigma, St. Louis, Mo.

With respect to the color developer, it should be noted that any developers which will demonstrate colorimetrically the release of a chromophore ca be utilized in the practice of the invention. Illustrative examples include, fast garnet-gbc salt (Sigma Chemicals, St. Louis, MO) chemically designated o-aminoazotoluene-diazonium salt; fast blue; and an acidified solution of p-dimethyl-aminocinnamaldehyde.

In an alternative embodiment, proteolytic activity can be measured with a fluorogenic test substance such as 2-arginine-7-amino-4-trifluoromethyl coumarin derivatives. Proteolytic activity can therefore be demonstrated by the release of a fluorophore, as fluorescence which can be detected with a UV light source. Therefore, the term "chromophore" as used herein should be interpreted broadly to include a substance which absorbs visual or ultraviolet light or which fluoresces. The combination of a peptide substrate with a fluorophore will result in the production of a color change which is observable under UV light when the fluorophore is released. Observable will be the Stokes shift from fluorescent blue to green, for example.

In implementation of the above-described specific embodiment of the instant invention, the sampling technique included the removal of subgingival plaque. It should be appreciated that, in principle, the sampling techniques contemplated as being effective for the purposes of this invention can be any such method as is known in the art and can be applied to sample any tissue, fluid, or other specimen suspected of being diseased, and therefore includes, by way of example, subgingival plaque, gingival crevicular fluid, supragingival plaque, oral tissue, saliva or oral rinse expectorant, etc. Saliva or oral rinse expectorants, of course, could be concentrated prior to use by any known means. Preferably, the suspected periodontally-diseased specimen would be removed from either the most periodontally involved site per quadrant or from the mesial buccal approximal site of each first molar on patients without any obvious periodontal disease. Preferably, the supragingival plaque a the sample site would be removed and discarded. Filter paper, or the like, can be placed in the orifice of a gingival crevice to collect gingival crevicular fluid by capillary action. The protein is then eluted off of the filter paper and subjected to the chromogenic test substance.

The advantages and benefits associated with the use of the diagnostic test for periodontal disease according to the present invention are considered to be numerous and commercially significant. The diagnostic methods are useful in periodontal therapy as well as initial diagnosis of the presence or absence of an anaerobic infection. It is believed that the present invention is particularly useful in identifying common periodontitis, namely chronic destructive periodontitis, wherein the patient displays significant increases in spirochetes, *T. denticola, B. gingivalis, B. forsythus*, and *C. gingivalis*. The diagnostic test is also helpful for quantitative evaluation of various stages of treatment of the disease and can aid in a determination of whether treatment has been adequate and whether additional modalities of treatment ar warranted. The method is particularly suited for use at periodic maintenance visits to determine whether retreatment is necessary.

It should further be appreciated that for purposes of this invention, the diagnostic test is not limited to human periodontal disease, but can be equally applied to the diagnosis of the disease in mammals in general. As such, the methods of the present invention will find application in the veterinarian sciences.

Although the invention has been described in terms of specific embodiments, and applications, persons skilled in the art can, in light of this teaching, generate additional embodiments without exceeding the scope or departing from the spirit of the claimed invention. Accordingly, it is to be understood that the descriptions in this disclosure are proffered to facilitate comprehension of the invention and should not be construed to limit the scope thereof.

What is claimed is:

1. A method of diagnosing periodontal disease, the method comprising the steps of:
    (a) obtaining a sample of bacterial flora containing a multiplicity of microorganisms from the oral cavity of a mammal;
    (b) determining whether the total number of microorganisms in said multiplicity of microorganisms exceeds about 1,000,000 by subjecting said sample of bacterial flora to a nonspecific chromogenic test substance hydrolyzable by enzymatic activity of said multiplicity of microorganisms in said sample such that a chromophore will be released and observable provided that there are greater than about 1,000,000 of said microorganisms in said sample; and
    (c) measuring the proteolytic activity of said bacterial flora, in response to a positive indication in said step of determining, with a chromogenic test substance specific to a proteolytic enzyme produced by suspected periodontiopathogenic bacteria in said bacterial flora, said measurement being characterized by a positive indication in response to an elevated proportion of said periodontiopathogenic bacteria with respect to the total number of microorganisms in said multiplicity of microorganisms, providing that said total number of microorganisms is greater than about 1,000,000, said elevated proportion indicates a diagnosis of periodontal disease.

2. The method of claim 1 wherein said nonspecific chromogenic test substance in said step of determining is hydrolyzable by a phosphatase.

3. The method of claim 2 wherein said phosphatase is selected from the group consisting of alkaline phosphatase and acid phosphatase.

4. The method of claim 2 wherein said chromogenic test substance in said step of determining is selected from the group consisting of p-nitrophenol phosphate, o-nitrophenol phosphate, and o-carboxyphenol phosphate.

5. The method of claim 1 wherein said chromogenic test substance in said step of determining is hydrolyzable by a peptidase.

6. The method of claim 1 wherein said peptidase is an amino peptidase.

7. The method of claim 5 wherein said chromogenic test substance is selected from the group consisting of N-L-proline-$\beta$-naphthylamide, L-luecine-$\beta$-naphthylamide, and L-phenylalanine-$\beta$-naphthylamide.

8. The method of claim 1 wherein said chromogenic test substance in said step of measuring is specific to proteolytic activity of an enzyme that acts on a substrate used for measuring trypsin, whereby a chromophore will be released and observable provided that said periodontopathogenic microorganisms are present in said sample in said elevated proportion.

9. The method of claim 8 wherein said chromogenic test substance in said step of measuring comprises a peptide substrate combined with a chromophore.

10. The method of claim 9 wherein said peptide substrate combined with a chromophore is selected from the group consisting of N-benzoyl-DL-arginine-2-naphthylamide and N-benzoyl-DL-arginine-p-nitroanilide.

11. The method of claim 1 wherein said step of measuring comprises the further step of adding a color developer.

12. The method of claim 9 wherein said peptide substrate combined with a chromphere is 2-arginine-7-amino-4-trifluoromethyl coumarin wherein a chromophore will be released and observable under UV light.

13. A method of diagnosing periodontal disease, the method comprising the steps of:
  obtaining a bacterial specimen containing a multiplicity of microorganisms from the oral cavity of a mammal;
  dispersing said bacterial specimen in a liquid medium;
  adding to said liquid medium a degradable chromophore-containing substrate susceptible to proteolytic enzymatic degradation caused by periodontopathogenic bacteria in said bacterial specimen;
  further adding to said liquid medium a nonspecific chromophore-containing substrate susceptible to enzymatic activity of said multiplicity of microorganisms in said bacterial specimens such that a chromophore will be released and observable provided that greater than about 1,000,000 of said microorganisms are present in said bacterial specimen;
  observing said liquid medium for a positive color change indicative of the presence of greater than about 1,000,000 of said microorganisms in said bacterial specimen; and
  in response to said positive color change in said step of observing, further observing said liquid medium for a further color change which is indicative of the presence of said periodontopathogenic bacteria in an elevated proportional concentration corresponding to a diagnosis of periodontal disease.

14. The method of claim 13 further including the step of adding a color developer to said liquid medium.

15. The method of claim 14 wherein said color developer is added to said liquid medium prior to performing said step of observing.

16. The method of claim 14 wherein said color developer is added to said liquid medium prior to performing said step of further observing.

17. The method of claim 13 wherein said degradable chromophore-containing substrate is specific to proteolytic activity of an enzyme that acts on a peptide substrate used for measuring trypsin.

18. The method of claim 13 wherein said nonspecific chromophore-containing substrate is specific to phosphatase activity, the color produced by the release of a chromophore due to said phosphatase activity being distinguishable from the color produced in response to proteolytic activity of periodontopathogenic bacteria.

19. The method of claim 18 wherein said liquid medium has a pH of between 5.0 and 8.5.

20. The method of claim 19 wherein said pH of said liquid medium is between about 5.0 and 6.0 and said nonspecific chromophore-containing substrate is specific to acid phosphatase.

21. The method of claim 20 wherein said nonspecific chromophore-containing substrate is o-carboxyphenol phosphate.

22. The method of claim 19 wherein said pH is between about 6.0 and 8.5 and said nonspecific chromophore-containing substrate is specific to alkaline phosphatase.

23. The method of claim 22 wherein said nonspecific chromophore-containing substrate is selected from the group consisting of o-nitrophenol phosphate and p-nitrophenol phosphate.

24. The method of claim 13 wherein said nonspecific chromsphere-containing substrate is specific to peptidase activity, the color produced by the release of a chromsphere due to said peptidase activity being distinguishable from the color produced in response to protolytic activity of periodontopathogenic bacteria.

25. The method of claim 24 wherein said peptidase activity is an aminopeptidase activity.

26. The method of claim 25 wherein said nonspecific chromophore-containing substrate is selected from the group consisting of L-proline-$\beta$-naphthylamide, L-leucine-$\beta$-naphthylamide, and L-phenylalanine-$\beta$-naphthylamide.

27. The method of claim 17 wherein said peptide substrate used for measuring trypsin is selected from the group consisting of N-benzoyl-DL-arginine-2-naphthylamide and N-benzyl-DL-arginine-p-nitroanilide.

* * * * *